United States Patent [19]

Alsberg

[11] 4,072,427
[45] Feb. 7, 1978

[54] FAULT INSPECTION SYSTEM

[75] Inventor: Dietrich Anselm Alsberg, Middletown, N.J.

[73] Assignee: Bell Telephone Laboratories, Incorporated, Murray Hill, N.J.

[21] Appl. No.: 709,308

[22] Filed: July 28, 1976

[51] Int. Cl.² ........................................... G01N 21/32
[52] U.S. Cl. ..................... 356/241; 358/87; 358/106
[58] Field of Search ............... 356/241; 358/87, 98, 358/106, 107

[56] References Cited

U.S. PATENT DOCUMENTS

| | | | |
|---|---|---|---|
| 3,320,359 | 5/1967 | Ikegami | 358/87 |
| 3,413,067 | 11/1968 | Froio | 356/241 |

OTHER PUBLICATIONS

Heinz, "Method of Checking Wall Imperfections", *Western Electric Technical Digest,* No. 19, pp. 31–32, July 1970.
Warters, "Millimeter Waveguide Scores High in Field Test", *Bell Laboratories Record,* pp. 401–408, Nov. 1975.
Carlin et al., "Waveguide Transmission Measurements and Analysis" *IEEE International Conf. On Comm., Conf. Record,* vol. 1, pp. (11-14)–(11-23) June 1976.

*Primary Examiner*—John K. Corbin
*Assistant Examiner*—Matthew W. Koren
*Attorney, Agent, or Firm*—John K. Mullarney

[57] ABSTRACT

A visual, fault inspection and fault location system for millimeter waveguide and the like comprises a cylinder of optically transparent material having a lens system mounted at one end thereof and a conical reflector at the other to permit the viewing of internal waveguide wall faults at right angles to the optical axis of the lens system. A video transmitter includes a camera tube positioned to receive images relayed by the lens system. The described optics assembly can be mounted on a self-propelled carrier, termed a "long distance mouse" because it travels through buried waveguide. An undistorted view of the interior wall of the waveguide is achieved by producing a polar scan in the camera tube and then displaying the resultant video signals at a remote receiver in accordance with a rectangular raster.

2 Claims, 8 Drawing Figures

IMAGE TRANSMITTER

IMAGE RECEIVER

FAULT INSPECTION SYSTEM

BACKGROUND OF THE INVENTION

This invention relates to a visual inspection and fault location system for millimeter waveguide and the like.

For certain fault conditions in installed millimeter waveguide, it is desirable to perform by remote control instrumentation a visual observation of a guide defect such as dielectric lining delamination, helix wire unwrap, welded coupling failure, etc. Video cameras have been designed which are small enough to be attached to a remote controlled self-propelled telemetry unit, termed a "long distance mouse" because it travels through buried waveguide. These video cameras typically use optics designed for the 16 millimeter movie picture format. Ideally, the lens system to use for this inspection purpose would be a "fisheye" lens with a viewing angle of at least 180°. As a matter of fact, fisheye lenses of this type were designed initially for the remote inspection of pipe lines and casings associated with oil drilling rigs. All commercially available fisheye lenses with a 180° or larger angle of view are expensive and, more importantly, too large in diameter to fit inside the WT4 millimeter waveguide (guide diameter is 60 mm). The cost of designing and producing a special fisheye lens for millimeter waveguide inspection is likely to be in the neighborhood of several hundred thousand dollars and thus would be prohibitive. Also, fisheye lenses suffer from image distortion, which makes images often difficult to interpret.

SUMMARY OF THE INVENTION

The primary object of the present invention is to visually inspect the interior wall of an elongated section of tubing, such as millimeter waveguide.

A related object is to provide a fault location and inspection tool which is comparatively simple in construction and of relatively low cost.

A still further object of the invention is to achieve an essentially undistorted view of the interior wall of millimeter waveguide and the like.

A fault location and inspection system in accordance with the present invention comprises a cylinder of optically transparent material having a lens system mounted at one end thereof and a conical reflector at the other end to permit the viewing of internal tubing (e.g., waveguide) faults at substantially right angles to the optical axis of the lens system. A video transmitter includes a camera tube positioned to receive images relayed by the lens system.

The video images from the camera tube will normally be distorted due to image contraction in the radial direction. However, an essentially undistorted view of the interior wall of the tubing can be obtained in accordance with the invention by producing a polar scan in the camera tube and then displaying the resultant video signals at a remote receiver in accordance with a rectangular raster.

In accordance with a feature of the invention the center portion of the cone of the conical reflector is eliminated and the resultant opening is used to provide a forward look into the tubing with the same lens system.

BRIEF DESCRIPTION OF THE DRAWINGS

The invention will be more fully appreciated from the following detailed description when the same is considered in connecton with the accompanying drawings, in which.

DETAILED DESCRIPTION

Figure 1:
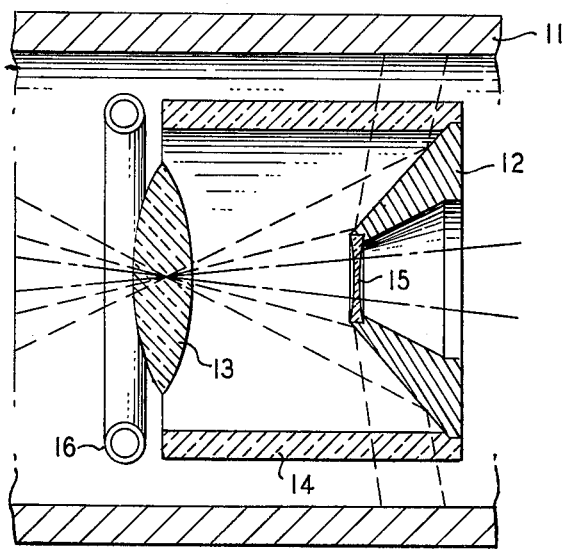
FIG. 1 is a simplified, sectional view of an optics assembly in accordance with a preferred embodiment of the present invention.

Turning now to FIG. 1 of the drawings, there is shown an optics assembly in accordance with the present invention which is useful in the visual inspection of the interior wall of tubing 11. More specifically, the fault inspection tool of the invention is intended for use with the WT4 millimeter waveguide which, as previously noted, is of too small a diameter to permit the use of commercial fisheye lenses; for a discussion of the WT4 waveguide see the article "Millimeter Waveguide Scores High in Field Test" by W. D. Warters, *Bell Laboratories Record,* November 1975, pages 401–408. In addition to its intended use with millimeter waveguide, however, the present invention may also be readily used in the inspection of just about all hollow tubing products (e.g., pipe lines and casings associated with oil drilling rigs), as well as in medical instrumentation such as cystoscopes, arterioscopes, etc.

The basic principle of the optics assembly is illustrated in FIG. 1. The conical reflector 12 is placed in front of the standard lens 13 thereby reflecting an image of the internal wall of the millimeter waveguide tubing 11 into the image plane of the lens. The optics assembly comprises an optically transparent cylinder 14 of glass or optical grade plastic with a lens system 13 (symbolically shown in FIG. 1 as a single lens) mounted at one end thereof and the conical reflector 12 supported at the other end. The wall of the cylinder 14 should preferably be thin to minimize optical aberrations, yet of sufficient rigidity to provide the requisite support for the lens system and the reflector. The reflector 12 has a cone angle of approximately 110°, although this is not critical, and since an aluminum reflecting surface is desirable the reflector can be made of aluminum or, alternatively, of glass with an aluminum coating. Following standard astronomical telescope practice, the reflecting aluminum surface would be protected by a thin evaporated SiO or $SiO_2$ coating.

The conical reflector is quite inexpensive to manufacture. For example, it is readily produced by roughing out an aluminum blank on a lathe and then lapping it to an optical finish on a standard lapping machine. Further, this reflector might then be used directly as part of a mold to produce a conical prism using a suitable optical grade transparent plastic, to which an aluminum coating is then applied.

As will be more evident hereinafter, the central region of the cone is of limited value for wall inspection purposes. Advantage is taken of this fact by eliminating the center portion of the cone for wall viewing purposes and instead using it as an opening to get a forward look into the waveguide with the same lens system. A negative lens 15 is placed into the conical aperture to correct for the focusing difference between the image of the wall and the forward look through the aperture in the conical reflector 12.

The transparent cylinder 14 is used primarily as a means for the in-line mounting of the lens system and conical reflector. However, when a fluorescent or incandescent lamp 16 is placed adjacent the end of the mounting cylinder, as shown in FIG. 1, the latter also serves as a light guide to provide the requisite illumination of the internal wall of the waveguide and of the forward area.

Figure 2:
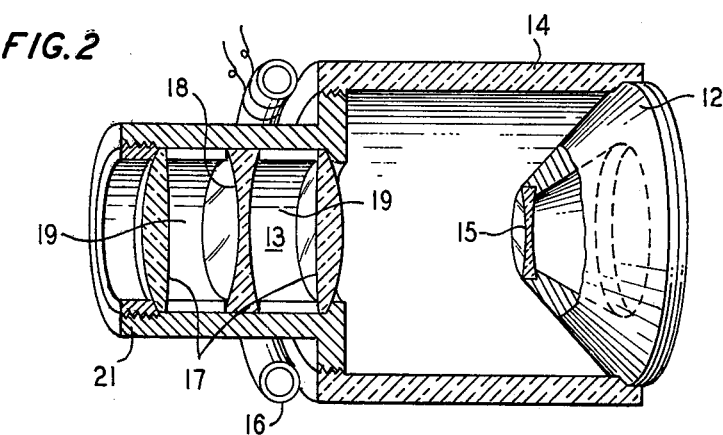
FIG. 2 is a perspective, sectional view of the optics assembly of FIG. 1.

FIG. 2 is a somewhat more detailed showing of the optics assembly of FIG. 1. As illustrated in FIG. 2, the lens system 13 is a conventional Cooke Triplet consisting of two positive crown elements 17 spaced apart from a negative flint element 18 by means of spacers 19. The lens holder 21 is screw mounted into the end of the transparent cylinder 14 The Cooke Triplet is probably the most widely used photographic lens, either in its original form or in one of its many derivatives. It is to be understood, however, that the invention is in no way limited to any particular lens and any of the standard photographic lenses used, for example, in commercially available 16 mm movie camera systems may be advantageously utilized herein.

A camera tube (not shown) is mounted in back of the lens system in a position to receive the images relayed by the lens. This camera tube may comprise a Vidicon tube, such as that used in PICTUREPHONE, or any other known image converting device of appropriate size.

The optics assembly of FIG. 2, the video camera and the image transmitter, to be described, are mounted on the head of a "long distance mouse" which is a remote controlled, self-propelled, telemetry unit. The long distance mouse is shown and described in the article "Waveguide Transmission Measurements and Analysis" by J. W. Carlin et al., *IEEE International Conference on Communications, Conference Record*, Vol. 1, June 1976, pages 11-19 to 11-23. The video signals from the camera tube are digitally encoded in the telemetry circuit of the mouse and then transmitted back down the waveguide to a remote video receiver. The long distance mouse and its telemetry comprise no part of the present invention and merely serve the purpose of facilitating the use of the fault inspection system of the invention over great lengths of waveguide. For short spans of waveguide (e.g., 20 feet or less) the long distance mouse can be dispensed with.

An odometer, calibrated in centimeters, is connected to a wheel of the long distance mouse and its output is telemetered back to the remote end of the guide. This permits a detected defect in the waveguide to be readily located. Also, conventional radar ranging techniques can be used for this purpose.

Figure 3:
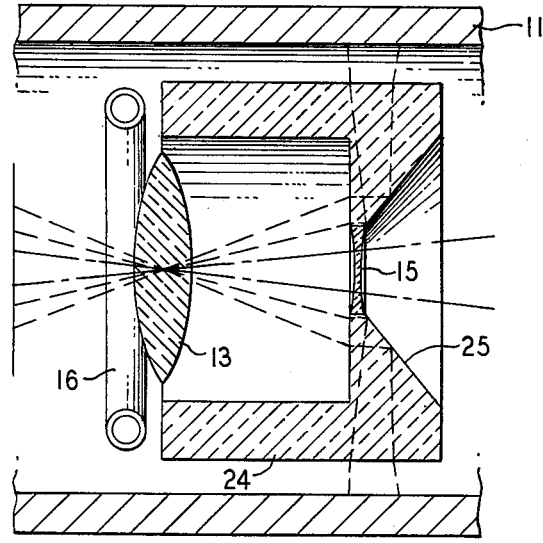
FIG. 3 is a simplified, sectional view of an optics assembly in accordance with another illustrative embodiment of the invention.

FIG. 3 shows another illustrative embodiment of an optics assembly in accordance with the invention. The mounting cylinder and conical reflecting prism are here molded as an integral unit 24, using glass or a suitable optical grade transparent plastic. The surface 25 of the tapered or conical hole is coated with aluminum to provide the requisite reflecting surface. Also, here again, a negative lens 15 is placed in the cone aperture to compensate for the focusing differentials. The remaining elements of the FIG. 3 assembly correspond to the similarly numbered elements of FIG. 1.

Figure 4:
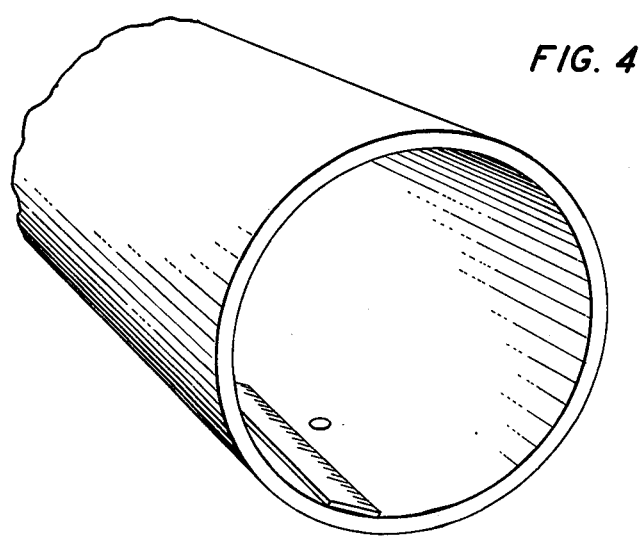
FIG. 4 is a view of a tubular waveguide with an internal fault or hole therein and a scale placed adjacent the hole.
Figure 5:
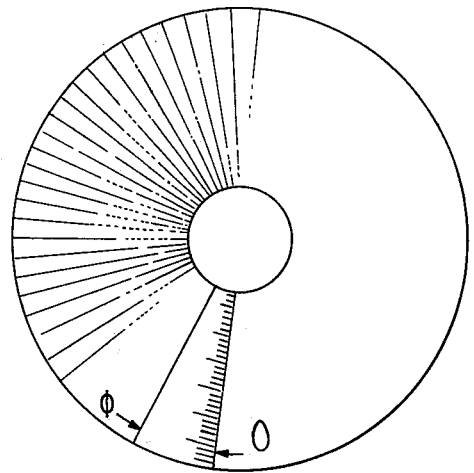
FIG. 5 illustrates the resultant image of the hole, the scale and the guide wall that is relayed by an optics assembly in accordance with the invention.

To provide an understanding of the optics involved with the use of a conical reflector, a piece of waveguide tubing such as illustrated in FIG. 4 has a hole drilled into the internal wall thereof and a scale graduated in millimeters is placed adjacent the hole. As the optics assembly of FIG. 2 is moved into the tubing to a point proximate the hole, a resultant image of the hole, the scale and the tubing wall will be relayed via the lens system 13. This resultant image is depicted in FIG. 5; the figure is, in fact, a reproduction of an actual photograph of the resultant image relayed by the lens system. As indicated in FIG. 5, the scale graduations are clearly readable and the wall features including the hole are clearly visible.

Considering FIG. 5, there is essentially no scale distortion in the longitudinal direction. This is evidenced by the graduations of the ruler image, wherein the mm. markers are essentially evenly spaced. This, of course, is to be expected. However, the image(s) will be distorted or compressed in the radial direction, and this image compression is greater the closer the image is to the center of the cone. For example, consider the image of the ruler or scale whose width describes a constant angle $\phi$. It will be evident that the length of an arc defined by angle $\phi$ (i.e., the apparent width of the ruler) is decreased or compressed the closer the arc lies to the center of the cone. This distortion or image compression should be rectified to permit a ready interpretation of wall faults. Furthermore, because of this image compression toward the center of the cone, the center portion of the cone is of limited value for inspection purposes and can be eliminated as heretofore described.

Figure 6:
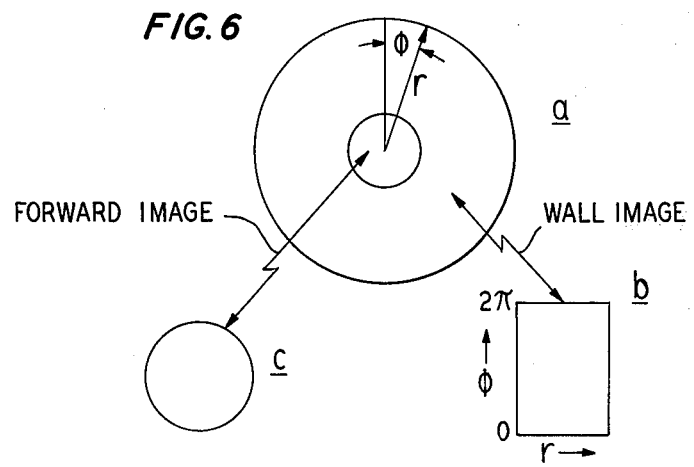
FIG. 6 shows diagrammatic figures useful in explaining the invention.

In accordance with the invention a rectified undistorted image can be obtained at a remote video receiver by producing a polar scan in the camera tube and then displaying that part of the image which corresponds to the guide wall on a rectangular grid with the ordinate proportional to $\phi$ and the abscissa proportional to the radial distance $r$, as shown in FIG. 6b. FIG. 6a represents the entire image incident on the camera tube and includes the forward look image and the wall image. The center part of the composite image which corresponds to the forward look can be separately displayed in its original polar coordinate form as indicated in FIG. 6c.

Figure 7:
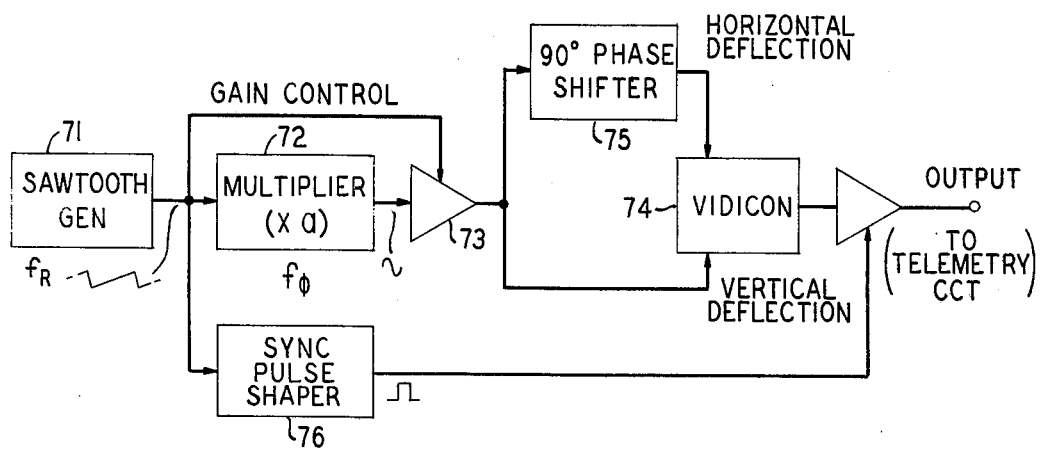
FIG. 7 is a simplified block diagram of an image transmitter in accordance with the present invention.

The circuitry for producing the requisite polar scan in the camera tube is shown in block diagrammatic form in FIG. 7. A sawtooth wave of frequency $f_R$ is produced by generator 71; $f_R$ is defined as the frame repetition rate and a typical frame rate of 60 frames per second can be advantageously utilized. An angular sweep frequency $f_\phi$ is derived from $f_R$ by a multiplier 72 with a multiplication factor of $a$, i.e., $f_\phi = a \cdot f_R$ where $a$ equals the number of circular lines in the picture raster. In the disclosed embodiment $a = 425$, i.e., there are 425 circular lines/frame. The angular sweep frequency ($f_\phi$) signal from the multiplier 72 is a sine wave. In order to control the radius of the circular sweep, the amplitude of the $f_\phi$ signal is controlled through the gain control sawtooth signal taken from the sawtooth generator. Thus, the $f_\phi$ signal is amplified in the amplifier 73, whose gain is linearly increased over the period of the sawtooth signal.

A circular sweep in the Vidicon camera tube 74 is produced by driving the vertical deflection plates, for example, directly from the output of the gain controlled amplifier 73 and driving the horizontal deflection plates with the same signal, but shifted by 90° in phase by phase shifter 75. Thus, an essentially circular trace or sweep is produced for the camera tube and because of the sawtooth gain control of amplifier 73 the trace or sweep in the camera tube increases in diameter throughout the period of a frame. Accordingly, in any one frame there are 425 concentric, esssentially circular lines in the scan of the camera tube and this pattern is repeated at the frame rate of 60 frames/second.

To provide a synchronization pulse for the video receiver a sync pulse of frequency $f_R$ is derived from the sawtooth generator 71 by means of the sync pulse shaper 76. This sync pulse is modulated onto the video signal from the Vidicon by signal intensification, or, as is more commonly done, by signal blanking. The composite output of the image transmitter of FIG. 7 is then sent to the telemetry circuit of the long distance mouse where it is digitally encoded for transmission to the remote receiver.

Figure 8:
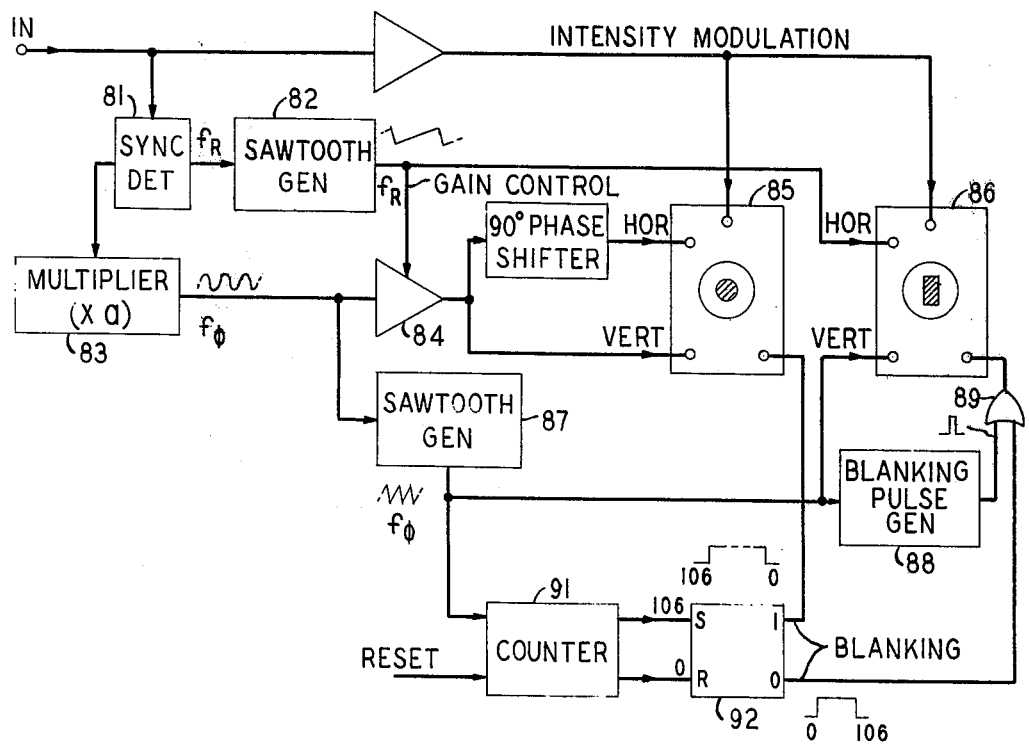
FIG. 8 shows a simplified schematic block diagram of an image receiver according to the invention.

After digital decoding, if the transmission signal had been encoded, the composite video signal is delivered to the input of the image receiver of FIG. 8. The sync pulses are detected by the sync detector 81 and used to regenerate the sawtooth $f_R$ and sine wave $f_\phi$ in the receiver. The output of the detector 81 is coupled to the generator 82 and the latter generates a sawtooth wave of frequency $f_R$. The angular sweep frequency $f_\phi$ is derived from the sync pulses by a multiplier 83 with a multiplication factor of $a$. The output of the multiplier is a sine wave. These operations have their counterpart in the transmitter.

For a polar display, of the forward look image, the deflection plates of the image display tube are again controlled as in the transmitter by shifting $f_\phi$ for one set of deflection plates by 90°. Also, the radius $r$ of the circular sweep is, here again, controlled through a gain controlled amplifier 84, to which the sawtooth wave $f_R$ is coupled. These operations produce a raster of concentric, essentially circular lines or sweeps in the display 85, all as previously described.

The part of the composite video image that corresponds to the guide wall is displayed in accordance with a rectangular raster in the video display 86. To this end, the $f_\phi$ signal from multiplier 83 is coupled to the sawtooth generator 87 which generates in response thereto a sawtooth of the same frequency $f_\phi$. This sawtooth wave of generator 87 is applied to one set of deflection plates, such as the vertical, of display 86. The sawtooth wave of frequency $f_R$ is applied to the other set of deflection plates. To blank the flyback trace for the $f_\phi$ sawtooth wave a short duration blanking pulse is derived from the same by generator 88 and it is delivered to the display 86 via OR gate 89. The video signal itself is used in the customary manner to intensify modulate the respective grids of displays 85 and 86.

From the foregoing description it will be evident to those in the art that for any one frame the rectangular raster will comprise 425 vertical lines; and, each essentially circular line of the scan of the camera tube will be displayed as a vertical line or scan in display 86. The successive video camera sweeps of incrementally increased diameter correspond to successive vertical lines or scans successively displaced toward the right in the rectangular raster.

The counter 91 and flip-flop 92 are used to generate blanking pulses that limit the polar display 85 to just the forward look image and the rectangular raster display 86 to the waveguide wall image. Let us assume that the forward look image has a radius of approximately one-quarter that of the entire image incident on the camera tube (see FIG. 5). Accordingly, about 106 circular traces or sweeps of the camera tube may be dedicated to the forward look image, while the remainder of the 425 circular scans are used to relay a video image of the waveguide wall. These numbers are only approximate and are used merely for illustrative purposes. The counter 91 counts through a 425 count cycle and then recycles. Counter 91 counts the sawtooth waves $f_\phi$ after it is first initialized by a reset sync signal, for example, from the sync detector 81. When the counter reaches a count of 106, a signal is sent to the flip-flop 92 to set the same to its "1" state. The flip-flop 92 then remains in this state until the counter recycles, at which time the flip-flop is reset to its "0" state. Thus, as illustrated in FIG. 8, the (0) output lead of flip-flop 92 is energized during the 0 to 106 count of the counter 91 and the (1) output is energized during the remainder of the counter cycle. The (0) output lead of the flip-flop delivers its energized signal to display 86 to blank the same during the forward look part of the received composite video image, and the (1) output lead is coupled to display 85 to blank out the wall image from display 85.

The foregoing explanation covers only those circuit aspects which provide the desired polar sweep in the transmitter and the polar and rectilinear sweeps in the receiver. The other requisite circuits which are customarily used in video cameras and video receivers need not be covered herein since they are amply described in the literature and known to those skilled in the video art. The circuit details of the various blocks shown in FIGS. 7 and 8 are also well covered in the literature.

The above described arrangement is considered to be merely illustrative of the principles of the present invention and numerous modifications thereof may be devised by those skilled in the art without departing from the spirit and scope of the invention.

What is claimed is:

1. A visual fault inspection system for waveguide and the like comprising a thin-walled hollow cylinder of optical transparent material, lens means mounted at one end of said cylinder, a conical reflector mounted in-line with said lens means at the other end of said cylinder to permit the viewing of objects substantially at right angles to the optical axis of the lens means, said conical reflector having the center portion of the cone eliminated to provide a forward look into the waveguide, a negative lens mounted in the center aperture of the conical reflector to compensate for focusing differentials, light means positioned adjacent the end wall of said cylinder at which said lens means is mounted to provide the requisite illumination of the internal wall of the waveguide and of the forward area, a video transmitter including a camera tube positioned to receive images relayed by said lens means, means for producing a polar scan in the camera tube, a video receiver including means for displaying signals obtained from the polar scanned camera tube in accordance with a rectangular raster, means for restricting the rectangular raster display to a display of only the internal wall image reflected by the conical reflector, a separate display means for displaying the forward look image in the original polar coordinate form, and means for restricting this latter display to a display of only the forward look image.

2. A visual inspection system as defined in claim 1 wherein the conical reflecting surface of said reflector is comprised of aluminum.

* * * * *